(12) United States Patent
Hanson et al.

(10) Patent No.: US 9,939,376 B2
(45) Date of Patent: Apr. 10, 2018

(54) METHOD FOR CALIBRATION-FREE SCANNED-WAVELENGTH MODULATION SPECTROSCOPY FOR GAS SENSING

(71) Applicant: The Board of Trustees of the Leland Stanford Junior University, Palo Alto, CA (US)

(72) Inventors: Ronald K. Hanson, Cupertino, CA (US); Jay B. Jeffries, Palo Alto, CA (US); Kai Sun, Stanford, CA (US); Ritobrata Sur, Stanford, CA (US); Xing Chao, Newark, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 949 days.

(21) Appl. No.: 14/367,420

(22) PCT Filed: Dec. 19, 2012

(86) PCT No.: PCT/US2012/070523
§ 371 (c)(1),
(2) Date: Jun. 20, 2014

(87) PCT Pub. No.: WO2013/096396
PCT Pub. Date: Jun. 27, 2013

(65) Prior Publication Data
US 2014/0336957 A1    Nov. 13, 2014

Related U.S. Application Data

(60) Provisional application No. 61/578,193, filed on Dec. 20, 2011.

(51) Int. Cl.
*G01T 3/00* (2006.01)
*G01N 21/39* (2006.01)
(Continued)

(52) U.S. Cl.
CPC .............. *G01N 21/39* (2013.01); *G01J 3/433* (2013.01); *G01J 3/4338* (2013.01); *G01N 33/0062* (2013.01); *G01N 2201/12* (2013.01)

(58) Field of Classification Search
CPC . G01N 21/39; G01N 33/0062; G01N 2201/12
(Continued)

(56) References Cited

U.S. PATENT DOCUMENTS 6,356,350 B1    3/2002  Silver et al.

OTHER PUBLICATIONS

Rieker et al. Calibration-free wavelength-modulation spectroscopy for measurements of gas temperature and concentration in harsh environments. Applied Optics, vol. 48, Issue 29, pp. 5546-5560 (2009).
(Continued)

*Primary Examiner* — David Porta
*Assistant Examiner* — Meenakshi Sahu
(74) *Attorney, Agent, or Firm* — Lumen Patent Firm

(57) ABSTRACT

A method of calibration-free scanned-wavelength modulation spectroscopy (WMS) absorption sensing is provided by obtaining absorption lineshape measurements of a gas sample on a sensor using 1f-normalized WMS-2f where an injection current to an injection current-tunable diode laser (TDL) is modulated at a frequency f, where a wavelength modulation and an intensity modulation of the TDL are simultaneously generated, extracting using a numerical lock-in program and a low-pass filter appropriate bandwidth WMS-nf (n=1, 2, . . . ) signals, where the WMS-nf signals are harmonics of the f, determining a physical property of the gas sample according to ratios of the WMS-nf signals, determining the zero-absorption background using scanned-wavelength WMS, and determining non-absorption losses using at least two of the harmonics, where a need for a non-absorption baseline measurement is removed from measurements in environments where colli- (Continued)

sion broadening has blended transition linewidths, where calibration free WMS measurements without knowledge of the transition linewidth is enabled.

13 Claims, 9 Drawing Sheets

(51) Int. Cl.
    *G01J 3/433*     (2006.01)
    *G01N 33/00*     (2006.01)

(58) Field of Classification Search
    USPC .................................................. 250/390.07
    See application file for complete search history.

(56) References Cited

OTHER PUBLICATIONS

Uehara. Dependence of harmonic signals on sample-gas parameters in wavelength-modulation spectroscopy for precise absorption measurements. Applied Physics Vo. 67 Jan. 1, 1998, pp. 517-523.

METHOD FOR CALIBRATION-FREE SCANNED-WAVELENGTH MODULATION SPECTROSCOPY FOR GAS SENSING

CROSS-REFERENCE TO RELATED APPLICATIONS

This application is a 371 of PCT/US2012/070523 filed on Dec. 19, 2012. PCT/US2012/070523 filed on Dec. 19, 2012 claims the benefit of U.S. Provisional Application No. 61/578,193 filed on Dec. 20, 2011.

STATEMENT OF GOVERNMENT SPONSORED SUPPORT

This invention was made with Government support under contract no. DE-FE0001180 awarded by the Department of Energy. The Government has certain rights in this invention.

FIELD OF THE INVENTION

The present invention relates generally to methods and devices for non-intrusive laser absorption sensing of gas temperature and species concentration using wavelength modulation spectroscopy. More specifically, it relates to improved wavelength modulation spectroscopy techniques suitable for measurements in high pressure gaseous environments with large non-absorption transmission losses.

BACKGROUND OF THE INVENTION

Laser absorption provides a non-intrusive method to sense temperature, pressure, and species concentrations in gas phase systems. Wavelength-modulation spectroscopy (WMS) is a method for sensitively detecting laser absorption and is typically performed by monitoring the transmitted laser power at the second harmonic of the modulation frequency (WMS-2f). The use of injection-current tuned diode lasers provides a signal at the first harmonic (1f) of the modulation frequency that is proportional to laser power.

For decades, sensitive tunable diode laser (TDL) absorption measurements have been performed with wavelength modulation spectroscopy (WMS) in a wide variety of practical applications. With its better noise-rejection characteristics through laser wavelength modulation strategies, WMS has long been recognized as the method of choice for sensitive measurements of small values of absorption, and thus is favored for trace species detection, measurements with significant noise, or both. Injection current-tuned TDL-WMS is attractive in systems with significant non-absorption attenuation of the optical transmission because it is possible to account for changes in laser intensity by normalizing the signals at even or odd harmonics of the modulation by the first harmonic signal.

Most early TDL-WMS applications were either in an atmospheric pressure open path or in a relatively low-pressure (P<2 atm) vessel, where the optimal modulation depths for achieving the strongest WMS signal were small and accessible within the tuning range of typical early TDLs. However, to achieve optimal WMS conditions for higher-pressure gas sensing, a larger modulation depth is required because the collisional width of the targeted transition is broadened. Based on a previous model describing the WMS-nf signals by Fourier analysis, TDL-WMS measurements with 2f detection at pressures to 10 atm using a large modulation depth were demonstrated.

Here, the concept of 1f-normalized WMS-2f considering the non-ideal modulation characteristics of injection current-tuned TDLs was discussed. Later, others developed a general protocol for 1f-normalized TDL-WMS measurements. The normalization scheme makes the WMS measurements independent of the laser intensity, and thus allows a calibration-free WMS measurement without the need to acquire the zero-absorption baseline during the absorption measurements. This benefit is important, since at pressures >10 atm where the transitions are strongly blended, it is generally difficult to find a near zero-absorption region near the targeted transition for the measurement of a direct absorption (DA) baseline. In addition, laboratory bench measurements indicate that WMS measurements have smaller uncertainties than DA for non-Lorentzian lineshape effects at high pressures, such as the breakdown of the impact approximation and line-mixing.

To meet more rigorous criteria for environmental-unfriendly emissions and to increase the energy efficiency, in-situ sensors are needed to optimize the performance of next-generation energy systems. Tunable diode laser absorption spectroscopy (TDLAS) offers potential for in-situ, non-intrusive, fast sensors for monitoring gas composition, temperature, pressure and velocity. With the emergence of the mature, reliable, narrow line-width wavelength-tunable diode lasers in the past two decades, such absorption sensors transitioned from laboratory measurements to use in conditions at harsh industrial facilities. Two schemes for TDL absorption have emerged for practical sensors, scanned-wavelength direct absorption (scanned-DA) and wavelength modulation spectroscopy (WMS).

Scanned-DA is most often used for its simple interpretation of the measured absorption signals in terms of the gas properties of temperature and composition, especially for facilities where the gas pressure is relatively low and for species with well-resolved absorption transitions. However, a scanned-DA measurement requires determination of a zero-absorption baseline, which is difficult to attain for high pressure environments where the collisional broadening blends neighboring transitions and eliminates regions of zero-absorption for the scan region of the laser. This can be even more challenging if the non-absorption transmission loss is time-varying, i.e. caused by beam scattering by coal particles in an entrained-flow coal gasifier, by bed particles in fluidized bed reactors, by the fly ash in a power plant economizer exit or in a waste incinerator. WMS using injection current-tuned diode lasers offers the potential of normalization of the 2f absorption signal by the 1f signal to account for time-varying non-absorption losses. This is possible because the signals for all the WMS harmonics are proportional to the laser power and the laser intensity modulation accompanying the injection-current modulation dominates the 1f signal for optically-thin conditions. This normalization enables quantitative WMS absorption measurements without determining a zero-absorption baseline. In addition, for WMS measurements performed with a modulation frequency larger than a few kHz, the detected harmonics can be isolated from the low-frequency noise. The bandwidth of the WMS measurements can be adjusted by the lowpass filter to balance the noise and the desired measurement time resolution. These are some of the features that make WMS an attractive alternative to DA for absorption measurements in harsh environments.

Although WMS has advantages over DA in noise-rejection and does not require knowledge about the zero-absorption baseline, previous calibration-free WMS measurements require laboratory characterization of the laser tuning and an accurate spectral model including collisional broadening to interpret absolute gas properties from the measured WMS signals. Although there is a large literature of models to simulate WMS spectra, it is common for a typical WMS model to involve many mathematical expressions, which can make the WMS technique complicated. The model becomes even more complex when the analytical WMS signals are explicitly expressed for an explicit lineshape function. Thus, almost all models have been simplified by assumptions. For example, some models can only be used for conditions where the intensity modulation is not important, the modulation depth is small, or the modulation frequency is low. Others are only accurate when the intensity modulation is linear, and may not be suitable for external cavity lasers where the non-linearity in intensity modulation can be large, or in a system where the optical components are wavelength dependent, such as a semiconductor optical amplifier or interference in the transmission produced by etalons from optical components with parallel surfaces. These complexities and limitations are even more pronounced for scanned-wavelength modulation spectroscopy where the laser-dynamics cannot be accurately described by a Fourier series of only one modulation frequency.

Most calibration-free WMS methods require an accurate estimation of the collisional broadening database, involving a heavy workload to pre-measure the broadening coefficients of the selected transitions at a range of temperatures. The total lineshape is then estimated based upon the measured coefficients of each broadening partner, and the gas composition in the target application. This estimation can have large uncertainties when the gas composition cannot be accurately known.

What is needed is a unified, accurate approach to determine the WMS absorption lineshape spectra at multiple harmonics of the modulation frequency for providing a sensor that is appropriate for high-pressure, particulate laden environments, e.g., in order to allow control of commercial coal gasification, where a need for a non-absorption baseline measurement is removed from measurements in environments where collision broadening has blended transition linewidths, where calibration free WMS measurements without knowledge of the transition linewidth is enabled.

SUMMARY OF THE INVENTION

A method of calibration-free scanned-wavelength modulation spectroscopy (WMS) absorption sensing is provided that includes obtaining absorption lineshape measurements of a gas sample on a sensor using 1f-normalized WMS-2f, where an injection current to an injection current-tunable diode laser (TDL) is modulated at a frequency f, where a wavelength modulation of the TDL and an intensity modulation of the TDL are simultaneously generated, extracting using a numerical lock-in program on an appropriately programmed computer and a low-pass filter with an appropriate bandwidth WMS-nf (n=1, 2, . . . ) signals, where the WMS-nf signals are harmonics of the f, determining a physical property of the gas sample according to ratios of the WMS-nf signals, determining the zero-absorption background using scanned-wavelength WMS, and determining non-absorption losses using at least two of the harmonics, where a need for a non-absorption baseline measurement is removed from measurements in environments where collision broadening has blended transition linewidths, where calibration free WMS measurements without knowledge of the transition linewidth is enabled.

According to one aspect of the invention, the physical properties of the gas sample can include arbitrary species, pressure, or temperature. In one aspect, the pressure of the gas sample is determined according to ratios $2f_{peak}/4f_{peak}$ and $2f_{peak}/6f_{peak}$.

According to another aspect of the invention, for measurements preformed with a modulation frequency f>2 kHz, the detected harmonics are isolated from a lower frequency noise, where the low frequency noise is <1 kHz.

In a further aspect of the invention, a gas number density is determined by simultaneous measurements that include an absorber mole fraction, gas pressure, and/or temperature.

According to another aspect of the invention, a first harmonic 1f signal is used to normalize a signal at harmonics greater or equal to 2f to account for the non-absorption transmission losses.

In yet another aspect of the invention, quantitative WMS absorption measurements are enabled without determination of a zero-absorption baseline.

In a further aspect of the invention, for scanned-wavelength WMS, a normalization with a mean magnitude of the 0f signal is used, where a mean variation on the 0f signal is decreased by averaging. In one aspect, a 0f-normalized 1f signal is used to infer gas properties in harsh environments comprising time-varying non-absorption transmission losses.

According to an aspect of the invention, a molecular absorbance is determined as a function of time during tuning of the TDL.

In a further aspect of the invention, both even and odd harmonics of the f are used to determine properties of the gas sample.

In another aspect of the invention, ratios the WMS-nf signals are a function of a transition lineshape of a specific the harmonic at a specific the wavelength, where the ratio is independent of an integrated absorbance and a transmitted laser power. In one aspect, the physical property comprises a collision width, where a total pressure of a gas mixture is proportional to a collision broadening width of the transition lineshape.

According to another aspect of the invention, an optically-thin condition isolated transition, a ratio of a peak signal magnitude from different the WMS harmonics is a function of a Doppler width and a collisional width, where broadening widths of the transition are obtained using a the signal ratio when the gas properties are not known, where the gas properties comprise composition, temperature, pressure and pathlength.

In another aspect of the invention, a ratio of $2f_{peak}$ to $4f_{peak}$ is used to infer a gas collisional width when the gas properties are unknown, where WMS two-line thermometry is used to infer the gas temperature, where an absorber mole fraction is determined by either transition used in the two-line thermometry.

DETAILED DESCRIPTION

Figure 1:
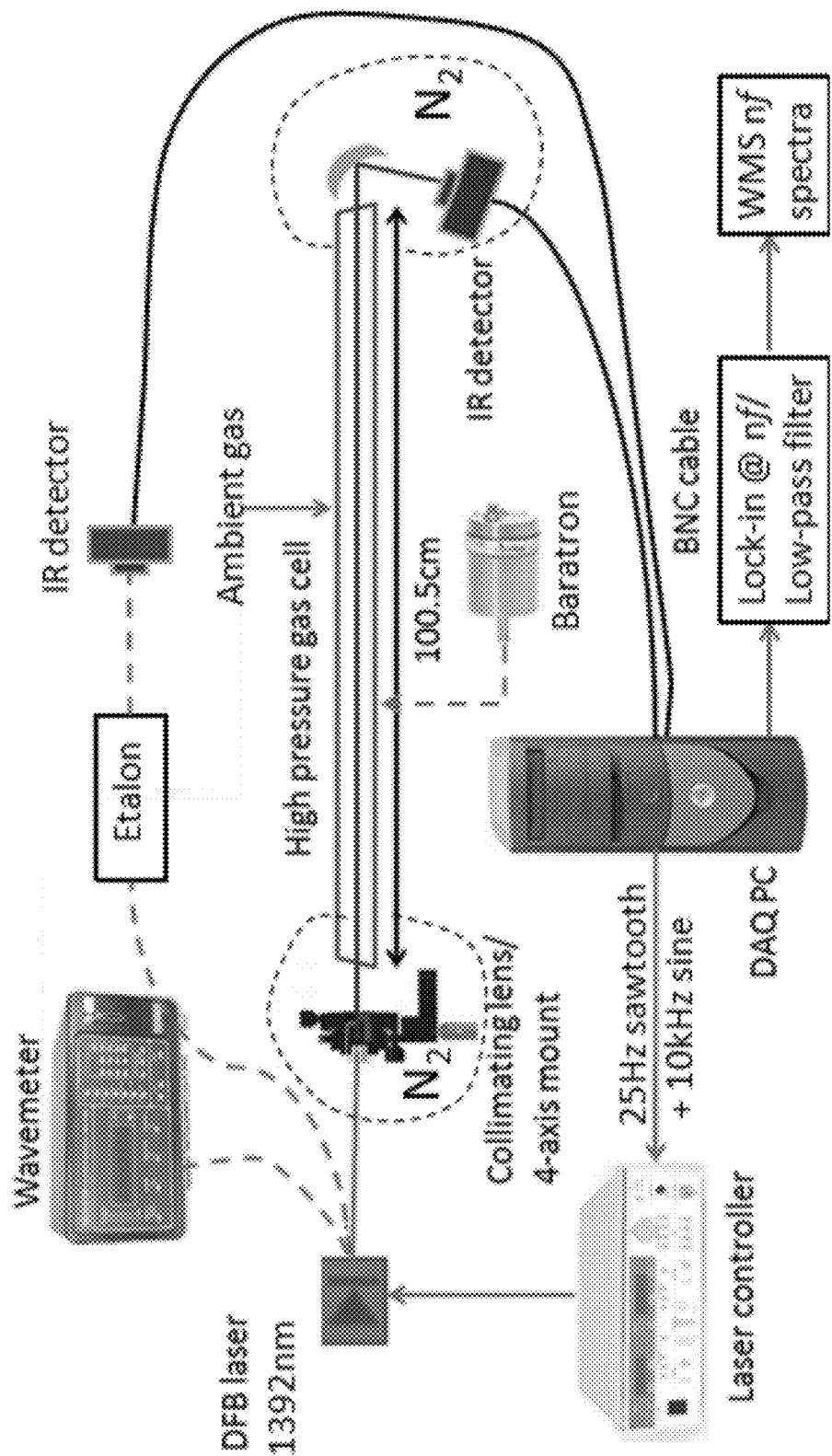
FIG. 1 shows a schematic of the experimental setup for measuring the WMS-nf spectra of the $H_2O$ transition near 7185.6 cm$^{-1}$, according to one embodiment of the invention.

The current invention provides a calibration-free wavelength-modulation spectroscopy (WMS) method for absorption sensing with injection-current-tuned diode lasers (TDLs). More specifically, a method of calibration-free scanned-wavelength modulation spectroscopy (WMS) absorption sensing is provided that includes obtaining absorption lineshape measurements of a gas sample on a sensor using 1f-normalized WMS-2f, where an injection current to an injection current-tunable diode laser (TDL) is modulated at a frequency f, where a wavelength modulation of the TDL and an intensity modulation of the TDL are simultaneously generated, extracting using a numerical lock-in program on an appropriately programmed computer and a low-pass filter with an appropriate bandwidth WMS-nf (n=1, 2, . . . ) signals, where the WMS-nf signals are harmonics of the f, determining a physical property of the gas sample according to ratios of the WMS-nf signals, and determining non-absorption losses using at least two of the harmonics, wherein a need for a non-absorption baseline measurement is removed from measurements in environments where collision broadening has blended transition linewidths and the zero-absorption baseline is determined by wavelength-scanned WMS to enable calibration free WMS measurements without knowledge of the transition linewidth.

According to one embodiment, the method is applicable for arbitrary species, gas pressure, temperature, modulation depth and harmonic order of the transmitted intensity, and can be used by fixed-wavelength or scanned-wavelength WMS methods. Instead of comparing the measured WMS signals with simulations using the mathematical expressions based on Fourier analysis, the method according to one embodiment simulates the transmitted laser intensity, then applies a lock-in program and a numerical lowpass finite-impulse response (FIR) filter to extract the nf components (WMS-nf) of the detector signal to compare with measurements. In one example described below, the method is validated using a distributed feedback (DFB) laser at 1392 nm to probe a $H_2O$ transition near 7185.6 $cm^{-1}$ at room temperature and atmospheric pressure conditions; WMS harmonics for 1 to 6 were extracted. The simulated results are in good agreement with measurements, not only at transition line center, but for the entire WMS lineshape, offering the possibility of including the odd order harmonics in the absorption analysis. In conditions of optically thin absorption for an isolated transition, the ratio of the WMS peak signals from different harmonics becomes a function only of the transition lineshape. To leverage this property, a pressure sensor is provided using the $2f_{peak}/4f_{peak}$ and $2f_{peak}/6f_{peak}$ signal ratios and demonstration experiments found less than 2% difference was found when compared to a baratron for a pressure range from 100 torr to 753 torr at room temperature; measurements in gasifier environments extended these demonstration experiments to 350 psia, even with non-absorption scattering losses reducing the laser transmission to less than $10^{-6}$ of the incident intensity. In addition, an approach to realize calibration-free WMS measurements without the necessity to pre-estimate or pre-measure the collisional-broadening of the probed transition is provided, which makes the WMS measurements calibration-free.

The range of temperatures and pressures for measurement depend on the structure of the absorption spectrum, which makes these ranges depend on chemical species as well as what potential interference absorption might be in the said gas sample. For example the method of the current invention was demonstrated for water vapor absorption in the near infrared from 0.01 psia to 350 psia and to temperatures to 2000K in a coal gasifier. The values were limited by the demonstration system available and not by the method. Other species have different limiting values depending on the structure of their absorption spectrum.

In the example described below, the method was validated by measuring the WMS absorption spectrum of a $H_2O$ transition near 7185.6 $cm^{-1}$ at various pressures from 100 torr to 753 torr at room temperature using a DFB diode laser (NEL). Since the higher harmonics are more sensitive to the lineshape function, a method that combines WMS signals at different harmonics to account for the collisional width of the transition will also be discussed. This new data reduction scheme can provide gas number density by measuring the absorber mole fraction and gas pressure simultaneously. A method for calibration-free WMS without the necessity to pre-measure or estimate the transition broadening coefficients is also discussed.

For injection-current-modulated diode lasers, simultaneous intensity modulation and wavelength modulation are observed typically. Many WMS models expand the intensity modulation into a Fourier series and retain the number of terms needed to approximate the WMS signal depending on the laser architecture and modulation depth. In one embodiment of the current invention, a method to get the WMS signals at different harmonics of the modulation frequency is provided. Instead of using complex mathematical expressions, the method simulates the received signal on a photodiode detector with modest mathematics, and uses a matlab lock-in program and a numerical lowpass filter to post-process the simulated detector signal to extract the set of WMS-nf signals for each harmonic n of the modulation frequency f.

For most TDL measurements, the signal (in voltage) received on the detector can be expressed as:

$$S_D = G \cdot I_{bg}(t) \cdot \exp[-\alpha(v(t))] + S_{offset}, \quad (1)$$

where G is the gain or optical-to-electrical conversion coefficient of the detector, $I_{bg}(t)$ is the laser intensity impinging on the detector when absorbers are absent, $\alpha$ the absorbance (or optical depth) of the gas media, $v$ the laser light frequency (or wavelength), t the time during the measurement and $S_{offset}$ the DC offset of the detector caused by the sum of optical emission and the dark current of the photodiode. To simulate the detector signal precisely, three factors must be well determined. First is the background signal on the detector $G \cdot I_{bg}(t) + S_{offset}$, which can be measured with the absence of absorbers along the line-of-sight (LOS) of interest. Second is the absorption spectra, $\alpha(v)$, determined by the spectroscopic parameters and gas properties though the Beer-Lambert's law:

$$\alpha(v) = \exp\left(-\sum_j S_j \cdot \phi_j(v) \cdot P \cdot x_i \cdot L\right), \quad (2)$$

where $S_j$ and $\phi_j$ are the linestrength and lineshape function of transition j, P is the total pressure of the gas, $x_i$ is the mole fraction of absorber i and L is the pathlength.

Third is the laser frequency tuning response to the injection-current tuning, $v(t)$, measured by using an etalon of known free spectral range (FSR) and a wavemeter or a reference cell filled with absorber with a known transition wavelength. For most applications, the injection current is modulated rapidly with a sine function at a frequency in the kHz to MHz range. A slow (normally from ~10 Hz to ~100 Hz) but wide (compared to the transition FWHM) near-linear scan of the center wavelength of the modulation is superposed on the modulation to extract a WMS lineshape. The resulted frequency response can be described as:

$$v(t) = \bar{v} + a \cos(2\pi f t + \varphi_v) + F(t), \quad (3)$$

where $\bar{v}$ is the laser frequency (or wavelength) without injection-current tuning, f the modulation frequency, $a$ [cm$^{-1}$] the modulation depth, $\varphi_v$ the phase of the frequency modulation, and F(t) the function describing the wide near-linear scan, normally a polynomial of three to four orders. When F(t)=0, the method is called fixed-wavelength WMS, which has the advantage of time-resolution determined solely by the lowpass filter bandwidth. When F(t)≠0, the method is called scanned-wavelength WMS and the time-resolution is limited to the scan frequency. The following discussions will be focused on the scanned-wavelength WMS, but it is noted that the current invention applies also to fixed-wavelength WMS.

The detector signal is then multiplied by cos(n·2π f t) to shift the X-component (or real component) of the detector signal at nf frequency to zero frequency. A lowpass filter with a bandwidth less than f/2 is used to extract this component, which is called the X-component of the WMS-nf signal:

$$X_{nf} \colon S_D \cdot \cos(n \cdot 2\pi f_m t) \to \text{lowpass filter}. \quad (4)$$

Similarly, the Y-component (or imaginary component) of the WMS-nf signal can be obtained by multiplying the detector signal by sin(n·2π $f_m$t)

$$Y_{nf} \colon S_D \cdot \sin(n \cdot 2\pi f_m t) \to \text{lowpass filter}. \quad (5)$$

The absolute magnitude of the WMS-nf signal can be obtained as:

$$S_{nf} = \sqrt{X_{nf}^2 + Y_{nf}^2}. \quad (6)$$

Using this approach can make WMS measurements independent of the detection phase of the lock-in reference. For cases where the WMS background signals are large compared to the WMS absorption signals; e.g., a small absorbance measurement at high pressures using a large modulation depth, the background signals can be subtracted to make the measured signal proportional to the absorbance, as:

$$S_{nf} = [(X_{nf} - X_{nf}^{BG})^2 + (Y_{nf} - Y_{nf}^{BG})^2]^{1/2}, \quad (7)$$

in which $X_{nf}^{BG}$ and $Y_{nf}^{BG}$ are the X and Y components of the WMS background signals at $n^{th}$ harmonics, which can be obtained as:

$$X_{nf}^{BG} = S_{BG} \cdot \cos(n \cdot 2\pi f t) \to \text{lowpass filter} \quad (8)$$

$$Y_{nf}^{BG} = S_{BG} \cdot \sin(n \cdot 2\pi f t) \to \text{lowpass filter} \quad (9)$$

where $S_{BG}$ is the detector background signal. The background signal causes an offset in the WMS signals, which is not necessary to subtract as long as it is present in the simulation and the measurement.

In harsh environments, the 1f signal can be used to normalize the nf signal, as:

$$S_{nf \, normalized} = \sqrt{\left[\left(\frac{X_{nf}}{R_{1f}}\right) - \left(\frac{X_{nf}^{BG}}{R_{1f}^{BG}}\right)\right]^2 + \left[\left(\frac{Y_{nf}}{R_{1f}}\right) - \left(\frac{Y_{nf}^{BG}}{R_{1f}^{BG}}\right)\right]^{B2}}, \quad (10)$$

where $R_{1f}$ and $R_{1f}^{BG}$ are magnitudes of the 1f-signal (without background subtraction) and the 1f-background signal, respectively. Since all harmonic signals are proportional to the laser intensity, this normalization can account for non-absorption transmission losses due to beam scattering and beam steering, or transmission variation due to mechanical vibration of the optics.

In some cases when the absorbance is large and the transition lineshape is a narrow isolated feature, the 1f signal can be small at specific wavelengths, which can result in a large spike in the 1f-normalized WMS-nf magnitude. This large normalized signal magnitude is an artifact of dividing by near zero, which artificially increases the sensitivity of the normalized WMS signal to the 1f harmonic. For scanned-wavelength WMS, this problem can be avoided using normalization with the mean magnitude of the 0f signal (DC signal after subtracting the detector offset) instead of the 1f. Although the 0f signal does not have noise-rejection features of the other harmonics, there can be many (~thousands) of samples for a typical scanned WMS measurement, thus the mean variation on the 0f signal can be decreased by averaging. The normalization strategy using 0f can also make it possible to use the 0f-normalized 1f signal to determine the gas properties in harsh environments, which can be attractive as the 1f signal typically has the largest SNR among all the harmonics.

Instead of simulating the WMS signal using Fourier analysis, the embodiment of the method described here simulates the laser intensity impinging on the detector directly, and uses a numerical lock-in program and low-pass filter with the appropriate bandwidth to extract the WMS signals at different harmonics. The method of the current invention avoids the need to explicitly characterize the laser intensity modulation and rather than an approximation, the recorded background signal $G \cdot I_{bg}(t) + S_{offset}$ contains all measured non-linear information about the intensity modulation, reflecting the modulation intensity characteristics of the whole optical system (i.e. this method accounts for etalon interference from optical components). In addition, since the numerical lock-in and low-pass filter used in the simulation are normally the same as the one used for post-processing the detected signal of WMS measurements, this method keeps the same non-ideal performance of lock-in and low-pass filter for both simulations and measurements.

Regarding the procedure and model validation, the new WMS-nf model of the current invention was validated by measurements of $H_2O$ WMS absorption lineshapes in a 100.5 cm long cell, installed with wedged sapphire widows on both ends to minimize etalon interference (FIG. 1). The cell was first evacuated to measure a background signal, then filled with the ambient $H_2O$ vapor present in room air and kept at a constant pressure, monitored by a baratron (0-1000 torr range, MKS). A DFB laser (NEL) near 1392 nm with single-mode fiber output was used to probe the $H_2O$ transition near 7185.6 $cm^{-1}$. The laser injection current was modulated with a sine function at 10 kHz, superposed on a sawtooth function at 25 Hz. Computer driven outputs (National Instruments PCI-6110) controlled the diode laser injection current (ILX Lightware LD-3900). After collimation, the laser beam travelled through the cell, and was focused onto a NIR photo-diode detector (Thorlab PDA-10CS, bandwidth: 775 kHz), used to convert the laser optical signal to voltage signal. The voltage signal was then sampled (same PCI-6110 card, 12 bits) at a sampling rate of 2.5 MHz. The WMS absorption lineshape signal was numerically post-processed by analyzing the simulated detector signal using matlab programs based on the described model. The numerical filter in the program was an FIR low-pass filter with a bandwidth of 2 kHz. The laser center wavelength without modulation was recorded (Burleigh WA-1000 NIR wavemeter) and the frequency response of the laser with modulation was measured using a fiber input/output etalon with 0.02 $cm^{-1}$ FSR (Micron Optics). The optical path external to the cell was purged with pure $N_2$ to eliminate the absorbance in the ambient environment.

Figure 2:
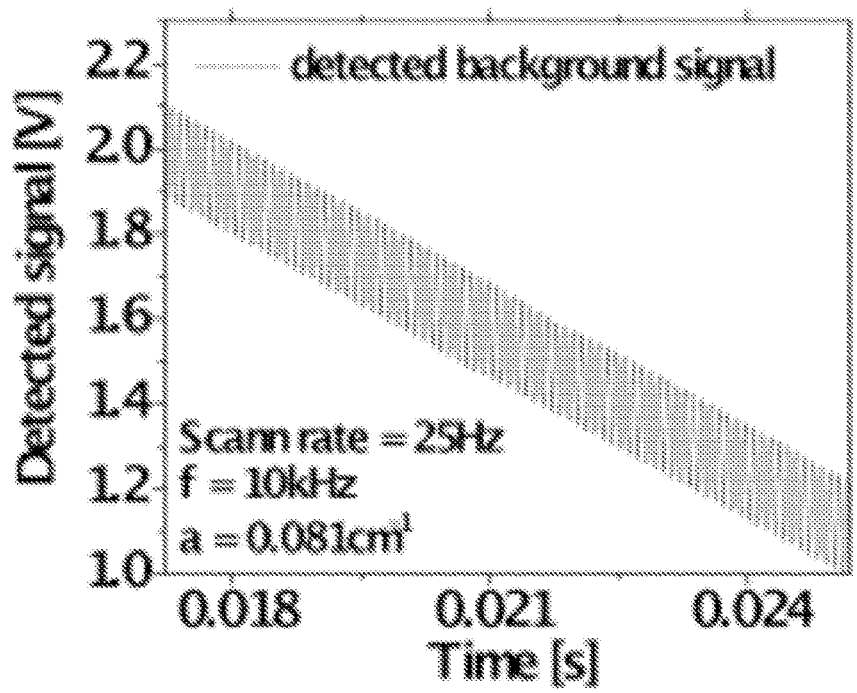
FIG. 2 shows measured laser intensity modulation signal in the absence of the absorber (scan rate=25 Hz, scan amplitude=2V, modulation frequency=10 kHz, modulation amplitude=0.1V), according to one embodiment of the invention.

The detector background signal $G \cdot I_{bg}(t) + S_{offset}$ from the laser intensity modulation was measured when the cell was empty (<0.01 torr); this can also be extracted from wavelength-scanned WMS without evacuating the cell. The measured signal is shown in FIG. 2.

Although the measurement was done when the external optical path was purged with pure $N_2$ to minimize the absorbance out of the cell, the method in the current embodiment is not limited by imperfectly purged regions. For example, even if no external purging was used, the absorption external to the cell could be considered as part of the background signal as long as the absorbance of $H_2O$ molecule in the atmosphere was stable during the measurement. The lack of a requirement for $N_2$ purge can reduce the system complexity for field measurements.

Figure 3:
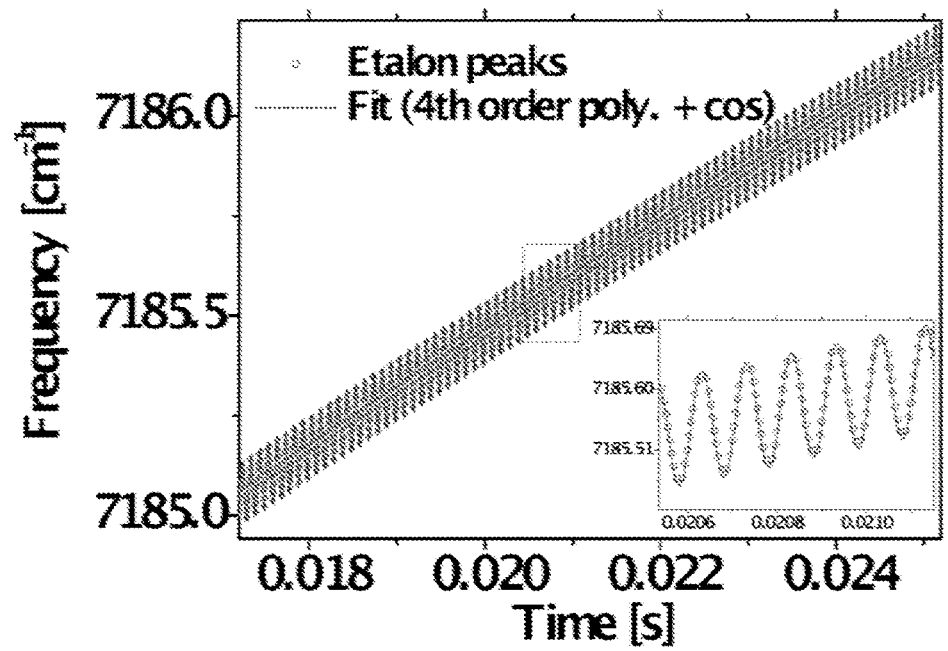
FIG. 3 shows measured frequency response to the laser injection-current tuning and its best fit, according to one embodiment of the invention.

For characterization of the laser frequency response $v(t)$, the laser frequency response to the injection-current tuning was measured by propagating the laser light though an etalon with 0.02 $cm^{-1}$ FSR and tracking the interference fringes peaks. FIG. 3 shows the measured frequency response to the injection-tuning scheme described above, and the best fit to the measurements.

$$v(t) = 7182.159 + 1.3775 \times 10^2 \cdot t + 2.4977 \times 10^3 \cdot t^2 - 1.1702 \times 10^5 \cdot t^3 + 1.3699 \times 10^6 \cdot t^4 + 0.081 \times \cos(2\pi \cdot 10^4 \cdot t - 2.0483)$$

Thus the modulation depth is 0.081 $cm^{-1}$ and the initial phase of the frequency modulation is −2.0483.

Regarding simulation of the absorption spectrum $\alpha(v)$, an accurate absorption spectrum, the spectroscopic parameters including the linestrength, $H_2O$—$H_2O$ broadening, and $H_2O$-Air broadening coefficients were pre-measured. Table 1 lists the measured parameters for the probed transition.

TABLE 1

Measured spectroscopic parameters for $H_2O$ transition near 7185.6 $cm^{-1}$ at 296 K.

| PARAMETER | MEASURED VALUE | UNCERTAINTY |
|---|---|---|
| LINESTRENGTH ($ATM^{-1}CM^{-2}$) | 0.0195 | <1% |
| $\Gamma_{SELF}$ ($CM^{-1}$) | 0.205 | <2% |
| $\Gamma_{AIR}$ ($CM^{-1}$) | 0.044 | <2% |

Figure 4:
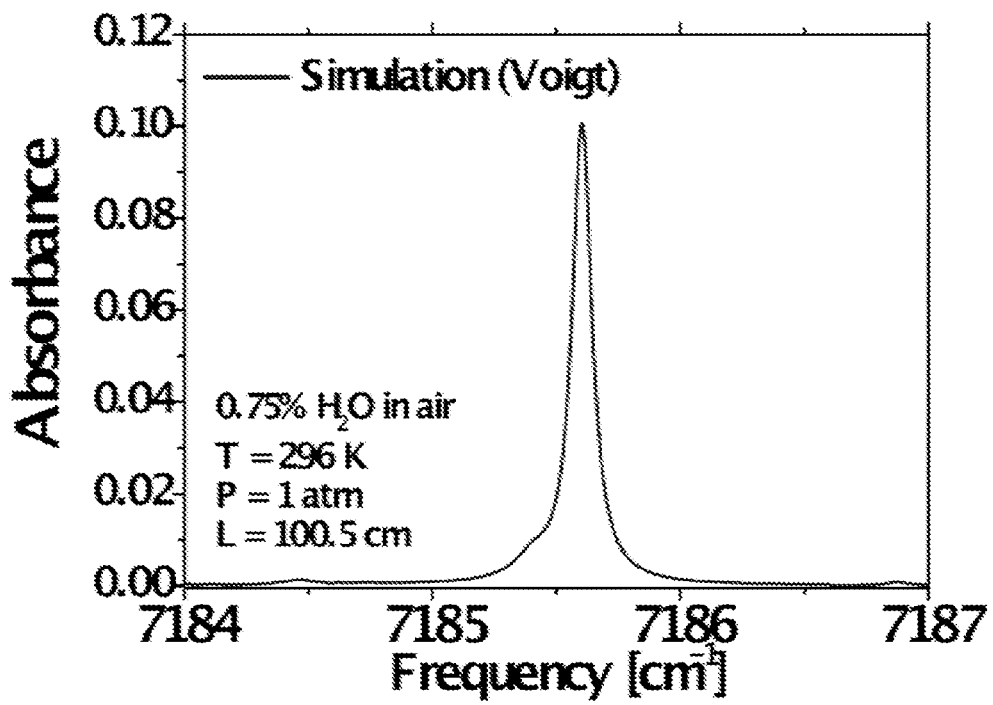
FIG. 4 shows simulated absorption spectra for $H_2O$ transition near 7185.6 $cm^{-1}$ (0.75% $H_2O$ in air, P=1 atm, T=296 K, L=100.5 cm), according to one embodiment of the invention.

The scanned-wavelength absorption for the expected cell gas properties (P=1 atm, T=296K, L=100.5 cm, 0.75% $H_2O$ in air) was then simulated using a Voigt lineshape function shown in FIG. 4.

Figure 5:
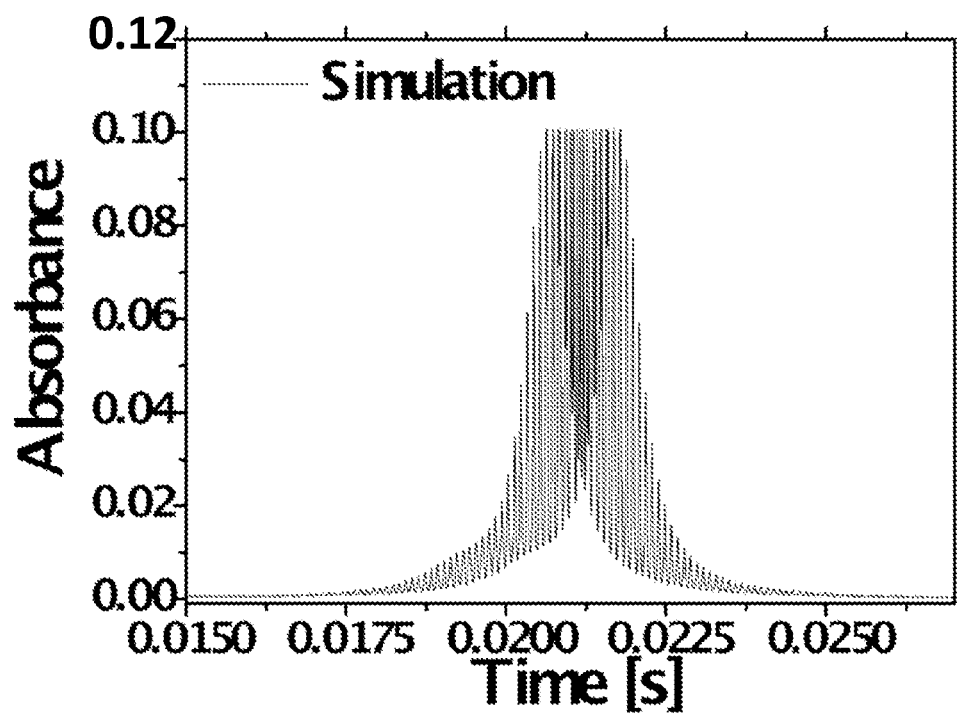
FIG. 5 shows simulated absorption spectrum for $H_2O$ transition near 7185.6 $cm^{-1}$ (0.75% $H_2O$ in air, P=1 atm, T=296 K, L=100.5 cm). Note constant peak values between 0.021 and 0.0225 s are real (not detector saturation) as the modulation is fast enough compared to the scan, according to one embodiment of the invention.
Figure 6:
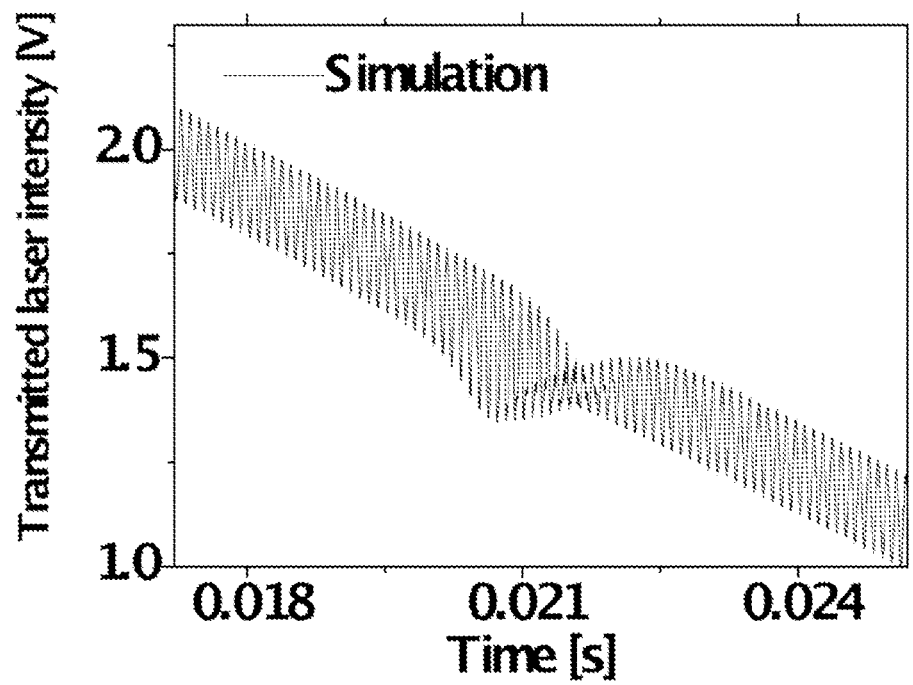
FIG. 6 shows simulated transmitted laser signal impinging on the photo-diode detector, according to one embodiment of the invention.

Simulation of the detector signal is provided using the data from FIG. 3 and FIG. 4, the molecular absorbance was calculated as a function of time $\alpha(v(t))$ during the tuning of the laser. The result is shown in FIG. 5; Due to the modulation of the laser wavelength, the absorbance reaches the peak value several times when the wavelength of the laser is at the line center of the probed transition. Using Eqn (1), the measured background results in FIG. 2 and the simulated results in FIG. 5, the transmitted laser intensity received on the detector can be simulated as shown in FIG. 6.

Figure 7:
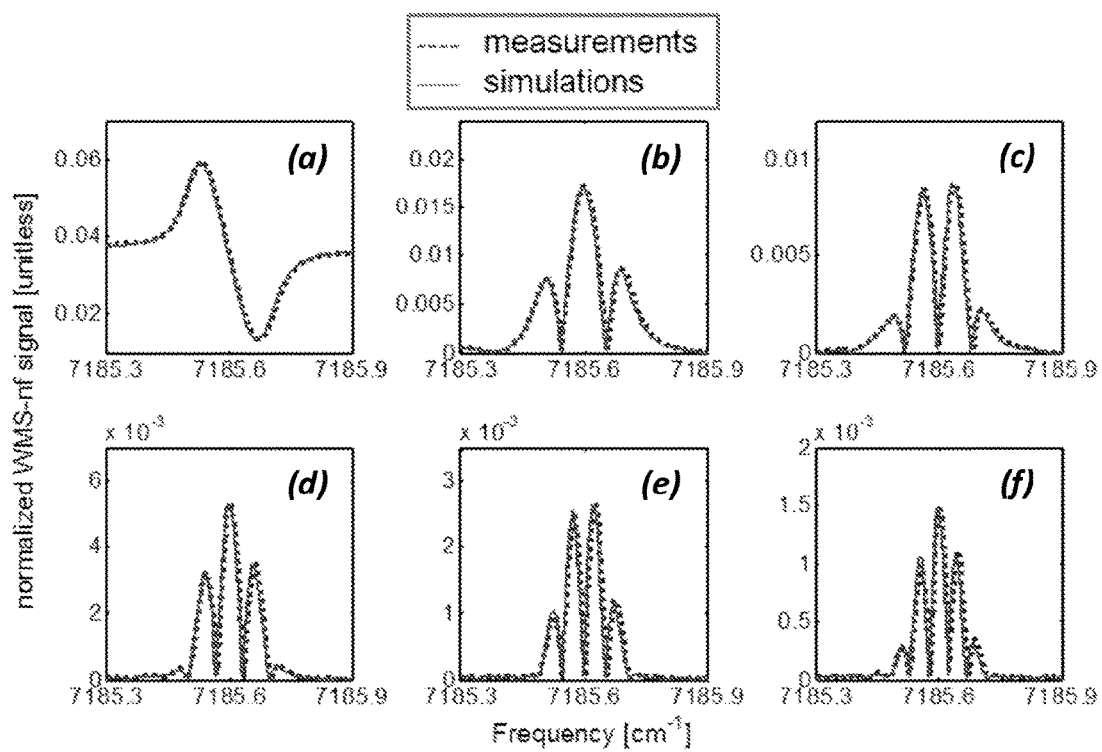
FIGS. 7a-7f shows simulated WMS-nf spectra with comparisons to measured spectra for $H_2O$ transition near 7185.6 $cm^{-1}$. The nf harmonics signals were normalized by the laser power impinging on the detector (T=296 K, P=1 atm, L=100.5 cm, a=0.081 $cm^{-1}$, f=10 kHz), according to one embodiment of the invention.

To obtain the WMS-nf spectra from the simulated detector signal FIG. 7 shows the simulated WMS nf spectra after processing the simulated detected signal (see FIG. 6) using a matlab lock-in program at nf frequency and a numerical FIR low-pass filter. The FIR filter is a polynomial of hundreds of orders, designed using the matlab filter design toolbox. In the same figure, the measured WMS-nf lineshape signals acquired when the cell was loaded with $H_2O$-air mixture at 1 atm are also shown. Both the simulated and measured nf spectra were normalized by the averaged laser power impinging on the detector (the DC or 0f component of the detector signal). The measured results have good agreement with the simulation, not only in the region near line center, but also at transition wings. This accuracy at wings provides the following opportunities for gas sensing: (1) both the even harmonics and the odd harmonics can be used to determine gas properties; (2) instead of using the peak magnitude of the spectra to determine the gas properties, the whole spectra of the probed transition is fitted to determine gas properties, similar to lineshape fitting for scanned-wavelength direct absorption. The $3^{rd}$ harmonic signal to determine gas properties is attractive since its peak magnitude is only slightly smaller than the $2^{nd}$ harmonic, but the signal-to-background ratio is much larger for the commercial DFB lasers used here. This potentially offers opportunity for improved measurements without decreasing the signal-to-noise ratio of the measurement with much reduced contribution by WMS background signals.

In using combinational harmonics to measure the transition lineshape function, the analytical expression for the X-component and Y-component of the WMS-nf signals can be expressed as:

$$X_{nf} = \frac{1}{2}G\bar{I}_0\left[H_n + \frac{1}{2}\sum_{k=1}^{\infty}(H_{n+k} + (1+\delta_{nk})H_{|n-k|})i_k\cos(\psi_k - k\cdot\psi)\right] \quad (11)$$

$$Y_{nf} = \frac{1}{2}G\bar{I}_0\left[\frac{1}{2}\sum_{k=1}^{\infty}(H_{n+k} - (1+\delta_{nk})H_{|n-k|})i_k\sin(\psi_k - k\cdot\psi)\right], \quad (12)$$

where $\delta$ is the Kronecker delta function, $i_k$ and $\psi_k$ are the $k^{th}$ order Fourier coefficient of the laser intensity modulation amplitude and phase, respectively, $\psi$ is the phase shift between the frequency modulation and the intensity modulation, and $H_k$ is the $k^{th}$ order coefficient of the Fourier expansion of the light transmission and can be expressed as:

$$H_k = \frac{1}{(1+\delta_{k0})\pi}\int_{-\pi}^{\pi}\tau(\bar{v} + a\cos\theta)\cos k\theta d\theta = \quad (13)$$

$$\frac{1}{(1+\delta_{k0})\pi}\int_{-\pi}^{\pi}\exp\left(-\sum_j S_j\cdot\phi_j(\bar{v}+a\cos\theta)\cdot P\cdot x_i\cdot L\right)\cos k\theta d\theta.$$

For optically-thin conditions:

$$H_k \approx \delta_{k0} + \frac{Px_iL}{(1+\delta_{k0})\pi}\int_{-\pi}^{\pi}\sum_j S_j\cdot\phi_j(\bar{v}+a\cos\theta)\cos k\theta d\theta. \quad (14)$$

And for condition that the absorption spectra of the interested wavelength region is mainly dominated by the targeted transition:

$$H_k \approx \delta_{k0} + \frac{SPx_iL}{(1+\delta_{k0})\pi}\int_{-\pi}^{\pi}\phi(\bar{v}+a\cos\theta)\cos k\theta d\theta, \quad (15)$$

Substituting (15) into (11) and (12), and after background subtraction we can obtain:

$$X_{nf} = SPx_iL\cdot\frac{1}{2\pi}G\bar{I}_0 \quad (16)$$

$$\left[\begin{array}{l}\frac{1}{(1+\delta_0)}\int_{-\pi}^{\pi}\phi(\bar{v}+a\cos\theta)\cos n\theta d\theta + \\ \sum_{k=1}^{\infty}\frac{i_k\cos(\psi_k-k\cdot\psi)}{2(1+\delta_{k0})}\int_{-\pi}^{\pi}\phi(\bar{v}+a\cos\theta)\cos(n+k)\theta d\theta + \\ \sum_{k=1}^{\infty}\frac{(1+\delta_{nk})i_k\cos(\psi_k-k\cdot\psi)}{2(1+\delta_{k0})}\int_{-\pi}^{\pi}\phi(\bar{v}+a\cos\theta)\cos|n-k|\theta d\theta\end{array}\right],$$

and $$Y_{nf} = SPx_iL\cdot\frac{1}{2\pi}G \quad (17)$$

$$\bar{I}_0\left[\begin{array}{l}\sum_{k=1}^{\infty}\frac{i_k\sin(\psi_k-k\cdot\psi)}{2(1+\delta_{k0})}\int_{-\pi}^{\pi}\phi(\bar{v}+a\cos\theta)\cos(n+k)\theta d\theta - \\ \sum_{k=1}^{\infty}\frac{(1+\delta_{nk})i_k\sin(\psi_k-k\cdot\psi)}{2(1+\delta_{k0})}\int_{-\pi}^{\pi}\phi(\bar{v}+a\cos\theta)\cos|n-k|\theta d\theta\end{array}\right].$$

Combining Eqn. (6) and after rearrangements of the terms, it is convenient to write the WMS-nf signal as:

$$S_{nf} = SPx_iL\cdot\frac{1}{2\pi}G\bar{I}_0 F(n, a, i_k, \psi_k, \psi, \bar{v}, \phi), \quad (18)$$

where F is a function of the parameters listed in the parenthesis. Note that the first parameter in the parenthesis is only related to the order of the harmonics and the four parameters that follow are the laser tuning parameters which are pre-measured and assumed to be unchanged here during the absorption measurements. Thus, for the tuning performance of a specific laser, the expression for the WMS signal can be further simplified to:

$$S_{nf}(\bar{v}) = SPx_iL\cdot\frac{1}{2\pi}G\bar{I}_0 F(n, \bar{v}, \phi). \quad (19)$$

Then the ratio of the WMS signals at different harmonics can be expressed as:

$$S_{nf}(\bar{v}_{nf})/S_{mf}(\bar{v}_{mf}) = \frac{F(n, \bar{v}_{nf}, \phi)}{F(m, \bar{v}_{mf}, \phi)}. \quad (20)$$

This ratio is independent of the integrated absorbance and the transmitted laser power. The ratio is a function only of the transition lineshape for specific harmonics at specific wavelengths. For most applications, including P<50 atm (750 psia) and temperatures where partition functions are known, the lineshape function can be described by a Voigt function (the Voigt function can be approximated by the Lorentzian function at high pressures, and by the Gaussian function at low pressures). Two broadening terms determine a Voigt lineshape function: The Doppler broadening width, $$v_D = v_0(7.1623\times 10^{-7})\left(\frac{T}{M}\right)^{1/2}, \quad (21)$$

where $v_0$ is the transition line center, M is the molecular weight in grams/mole, and the collisional broadening width:

$$v_c = P\cdot 2\sum_j x_j\gamma_{ij}(T), \quad (22)$$

in which $x_j$ is the mole fraction of species j in the gas mixture and $\gamma_{ij}(T)$ is the collisional broadening coefficient at temperature T of absorber i under the collisional perturbation by species j.

For a specific transition, the Doppler broadening width is a function of temperature only, but the collisional width is complicated, coupled with gas pressure, composition and pairs of collisional partners. On the other hand, this complexity enables the measurement of the gas properties via determination of the collisional widths.

One characteristic of WMS measurements is that the peak magnitudes of the absorption of harmonics are very sensitive to the transition broadening width. This sensitivity can be utilized to determine the gas properties that are related to the transition broadening width. For example, the total pressure of the gas mixture is proportional to the collisional broadening width of a transition:

$$P = v_c \cdot \frac{1}{2\sum_j x_j \gamma_{ij}(T)}, \qquad (23)$$

Figure 8:
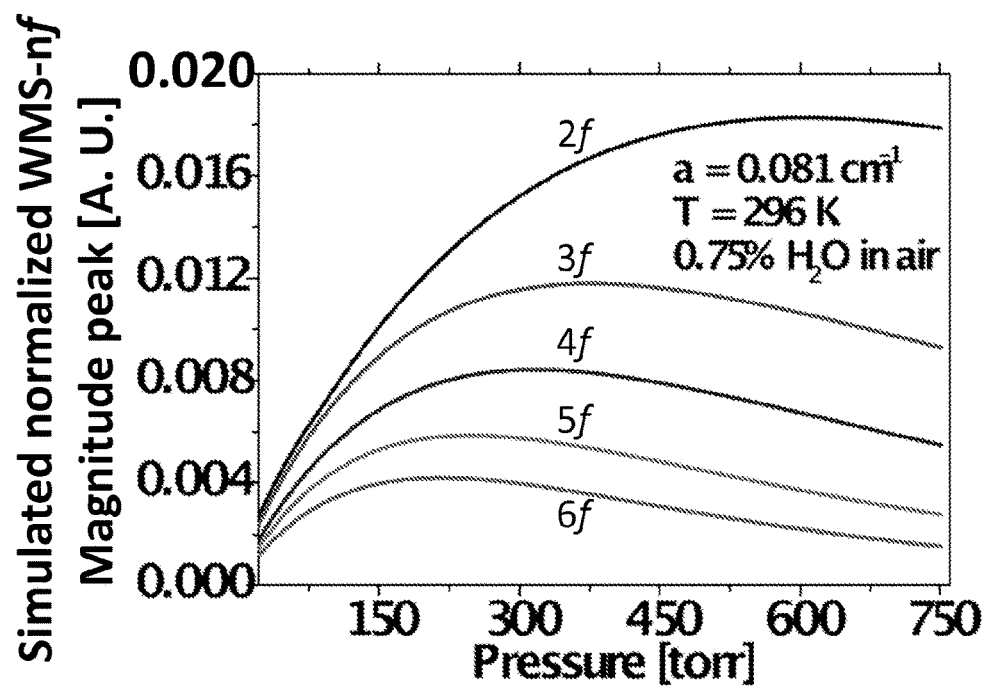
FIG. 8 shows simulated WMS-nf peak magnitude with pressure for $H_2O$ transition near 7185.6 $cm^{-1}$. (T=296 K, L=100.5 cm, a=0.081 $cm^{-1}$, f=10 kHz), according to one embodiment of the invention.

Under circumstances where $$\sum_j x_j \gamma_{ij}(T)$$

are not time varying, i.e. gas composition and temperature are stable, the gas pressure can be determined from the measured collisional broadening width. For a typical measurement condition, the higher order the WMS harmonic, the more sensitive it will be to the collisional broadening width. FIG. 8 shows the simulated WMS-nf peak magnitude in the lineshape spectra versus pressure. The shape of the WMS harmonic versus pressure is similar to that of the linestrength versus temperature. Similar to measuring the gas temperature using the two-line thermometry technique, the ratio of peak magnitudes of different harmonics can be used to determine the gas pressure. This strategy has the advantage for optically-thin conditions ($\alpha$<0.1), since all harmonics peak magnitudes are proportional to the integrated absorbance, the ratio is independent of the transition line strength and the absorber mole fraction (if the change of absorbers does not result in significant change in the broadening width).

Figure 9:
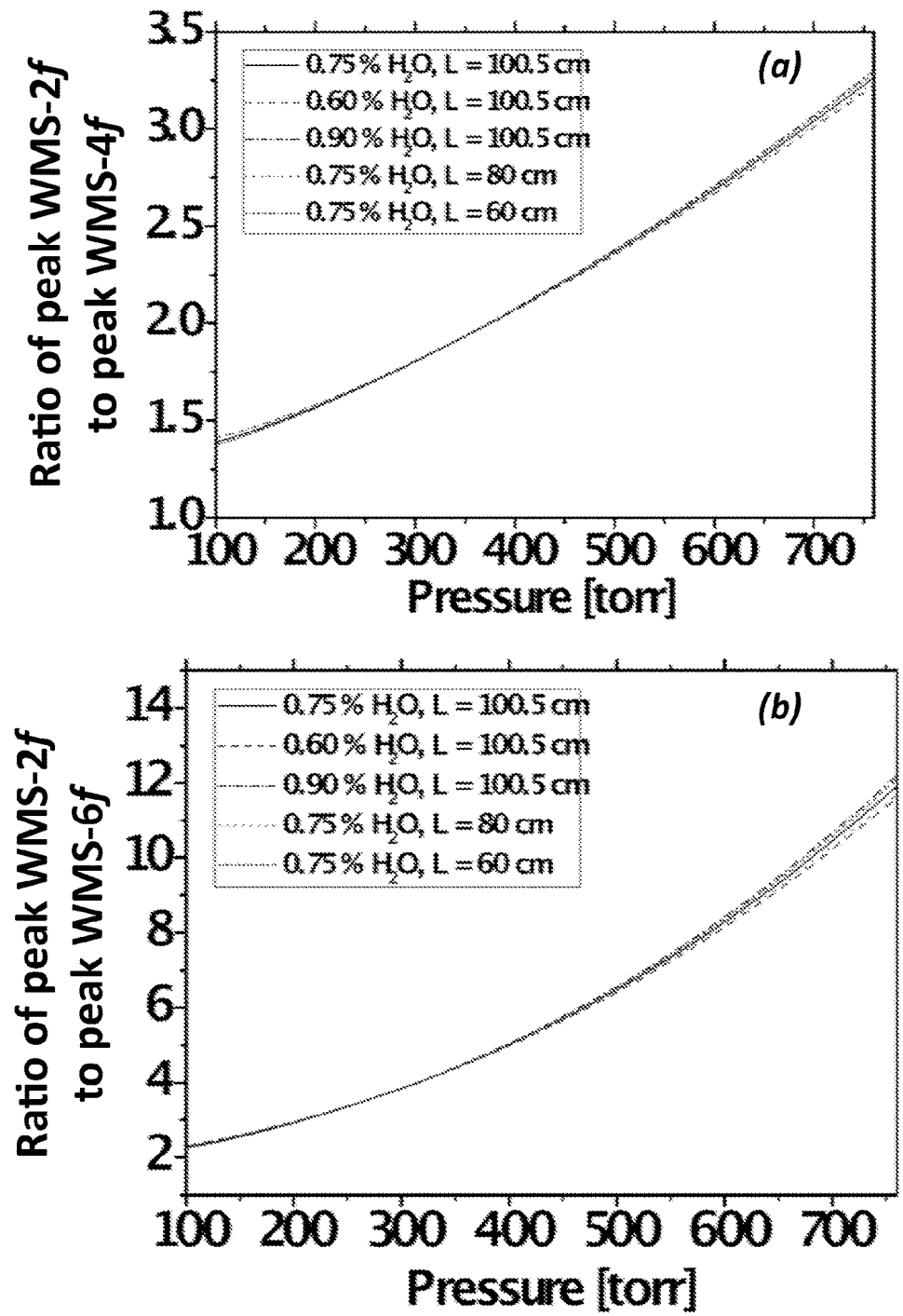
FIG. 9a-9b show simulated ratio of $2f_{peak}/4f_{peak}$ (9a) and $2f_{peak}/6f_{peak}$ (9b) with pressure for $H_2O$ transition near 7185.6 $cm^{-1}$. (T=296 K, a=0.081 $cm^{-1}$, f=10 kHz), according to one embodiment of the invention.

FIG. 9 shows the simulated ratio of $2f_{peak}/4f_{peak}$ (left) and $2f_{peak}/6f_{peak}$ (right) with pressure at room temperature for $H_2O$ transition near 7185.6 cm$^{-1}$ at different absorber mole fractions and pathlength conditions. As observed, a 20% change in the absorber mole fraction and pathlength results in less than 2% change in the ratio, indicating that the ratio is only sensitive to the gas pressure. Note the even harmonics have the same (or very close) peak positions (in wavelength), making this ratio strategy applicable to fixed-wavelength WMS as well. Since the ratio is independent of the laser intensity, this strategy is also attractive for pressure measurement in a harsh environment with time-varying non-absorption transmission losses.

Figure 10:
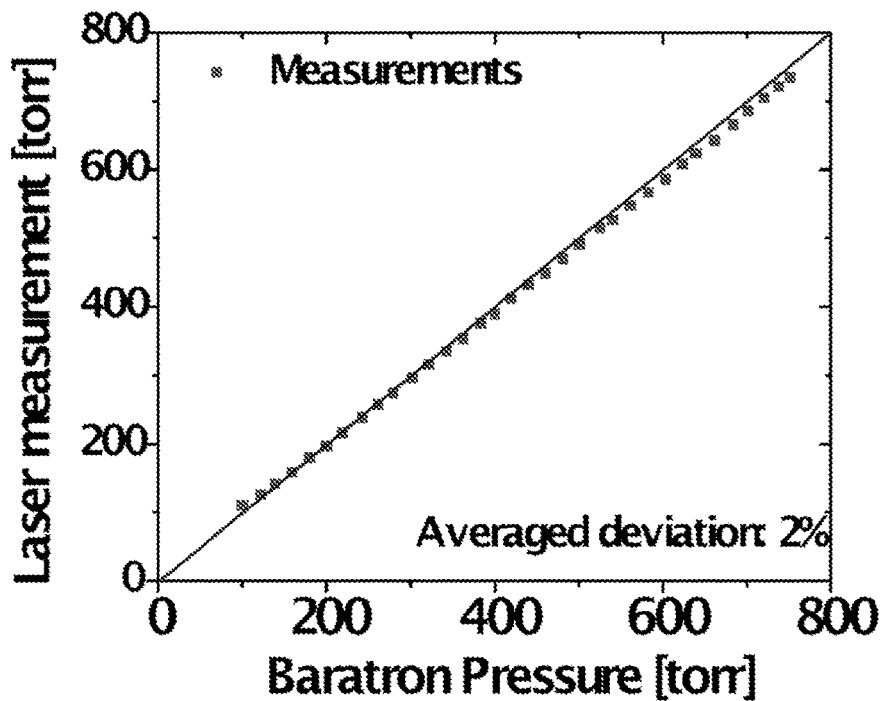
FIG. 10 shows measured gas pressure determined by $2f_{peak}/4f_{peak}$ (left) and $2f_{peak}/6f_{peak}$ (right). (T=296 K, L=100.5 cm, a=0.081 $cm^{-1}$, f=10 kHz), according to one embodiment of the invention.

Determination of pressure by the ratio of WMS-nf signals was demonstrated in the same experimental setup shown in FIG. 1, where the pressure in the cell was gradually increased from 100 torr to 753 torr. The laser measured results were compared with the baratron readings, for both $2f_{peak}/4f_{peak}$ and $2f_{peak}/6f_{peak}$ strategies as shown in FIG. 10. The discrepancies are less than 2% for both cases, demonstrating the feasibility of a pressure sensor using the ratio of signal peaks at different WMS harmonics.

One should note that since the absorber mole fraction can be determined by the 1f-normalized WMS-2f strategy once the pressure is known, this ratio of WMS-nf strategy offers the potential to determine the absolute absorber number density from WMS measurements of absorption without an independent measurement of pressure.

Regarding the absolute calibration-free WMS method, in the previous section, the pressure was determined from WMS signals for conditions with nearly constant collisional width per unit pressure. However, for most TDL absorption applications, pressure can be readily measured by various non-optical wall mounted sensors. In contrast, the broadening width of the transition is difficult to determine in the target reactive flow. For calibration-free WMS, the WMS signal magnitudes are sensitive to collisional broadening width and an accurate evaluation of the broadening coefficients is necessary. Although HITRAN provides an extensive database of spectroscopic parameters of transitions, it only reports the self-broadening coefficient and air-broadening coefficient, which are not sufficient for applications other than those in the atmosphere. Thus for most WMS calibration-free approaches, the broadening coefficients of the absorber perturbed by other species (including the absorber itself) need to be pre-measured at known temperature. The collisional width of the transition then can be estimated using Eqn. (22), assuming the gas mixture is well known.

However, such assumption may not be valid, especially for reacting applications, e.g., a coal-gasifier where the gas composition is complex and varies with process condition and input coal quality. To make precise calibration-free WMS in such conditions, the collisional width of the transition during the absorption measurements must be separately determined.

Figure 11:
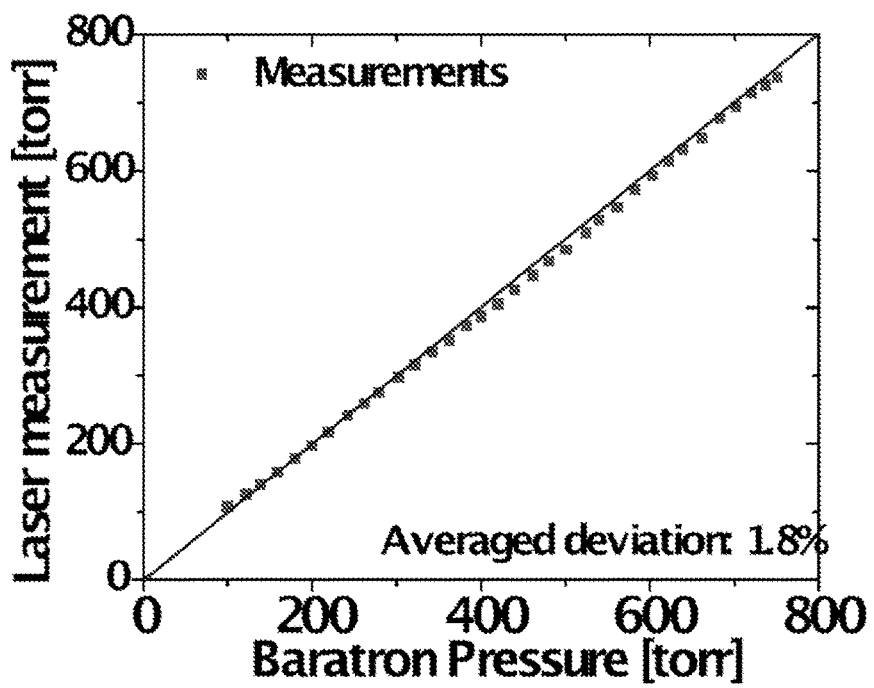
FIG. 11 shows simulated $2f_{peak}/4f_{peak}$ with collisional width at different pathlength, absorber mole fraction and pressure conditions (T=800 K, a=0.081 $cm^{-1}$, f=10 kHz), according to one embodiment of the invention.
Figure 12:
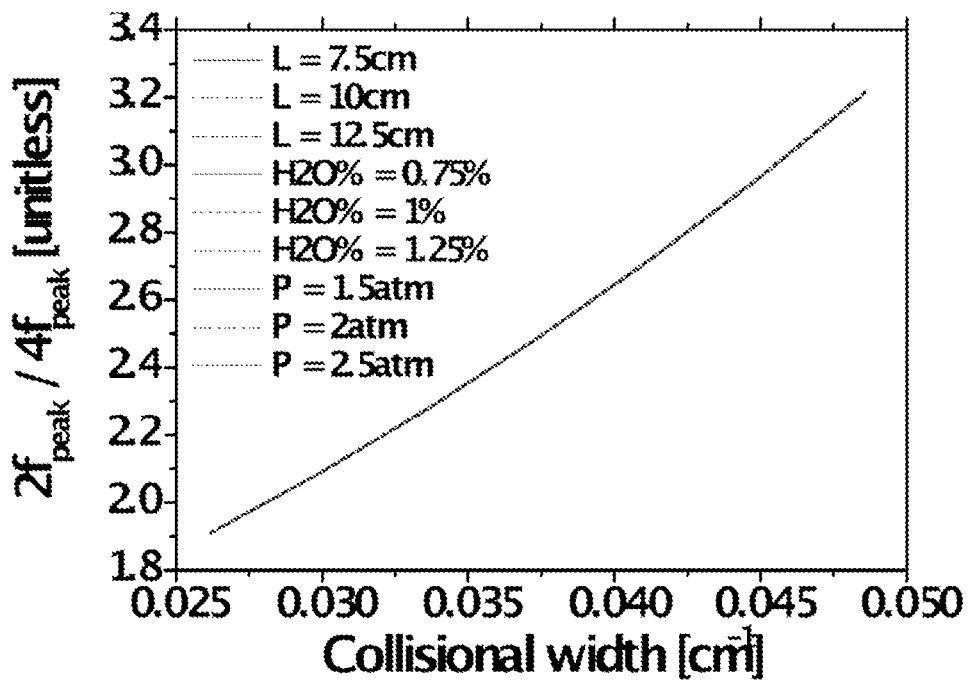
FIGS. 12-13 show simulated $2f_{peak}/4f_{peak}$ with collisional width at different temperature conditions (1% $H_2O$ in air, P=2 atm, L=10 cm, a=0.081 $cm^{-1}$, f=10 kHz, $v_D$=0.0343 $cm^{-1}$), according to embodiments of the invention.
Figure 13:
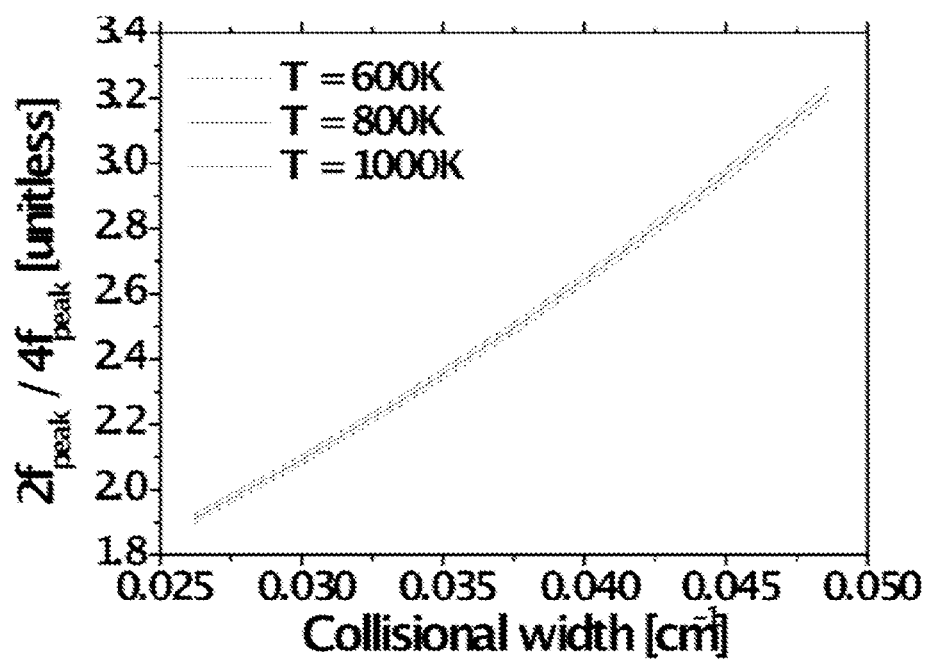

As Eqn. (20), for an optically-thin condition isolated transition, the ratio of the peak signal magnitude from different WMS harmonics is a function of the Doppler width and collisional width only. This suggests that the broadening widths of the transition can be obtained using the signal ratio even when the gas properties are not well known (e.g. composition, temperature, pressure and pathlength). FIG. 11 shows the variation of simulated ratio of $2f_{peak}$ to $4f_{peak}$ with collisional width at different pathlength, absorber mole fraction and pressure conditions when the temperature was kept constant. Since the temperature remained unchanged, the Doppler broadening width is constant as well. A 25% change in the pathlength, absorber mole fraction and pressure resulted in less than 0.1% change in the $2f_{peak}$ to $4f_{peak}$ ratio. Similar simulation was carried out as shown in FIGS. 12-13 for a 25% temperature change while other gas properties were kept constant. Despite the fact that the change of temperature resulted in a 12% change in the transition Doppler broadening width, the 25% uncertainty only caused less than 1% change in the signal ratio.

These results confirm the analytical result in Eqn. (20). In a practical measurement, the ratio of $2f_{peak}$ to $4f_{peak}$ can be used to determine the gas collisional width even when the gas properties are unknown. Once the collisional broadening widths are measured, WMS two-line thermometry can be used to determine the gas temperature, and then the absorber mole fraction can be determined by either transition used in two-line thermometry.

This strategy avoids the necessity in pre-calibrating the collisional width at known conditions of gas mixture, pressure and temperature and does not require the knowledge about the composition of the gas mixture, providing a significant improvement in the previous calibration-free WMS method. The method provides an alternative to the direct absorption commercial sensors, as this WMS scheme is calibration free with the advantage of improved noise rejection.

The selection of an optimal modulation depth to maximize the WMS signals cannot be determined in advance without an estimate of the broadening widths. Empirically, the modulation depths could be optimized during the field absorption measurements. Alternatively, one can scan the modulation depth in the measurement as well to ensure an optimal modulation depth is used.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of calibration-free scanned-wavelength modulation spectroscopy (WMS) absorption sensing, comprising:
   a. obtaining absorption lineshape measurements of a gas sample on a sensor using 1f-normalized WMS-2f, wherein an injection current to an injection current-tunable laser (TL) is modulated at a frequency f, wherein a wavelength modulation of said TL and an intensity modulation of said TL are simultaneously generated, wherein said WMS comprises fixed-wavelength or scanned-wavelength WMS methods;
   b. extracting using a numerical lock-in program on an appropriately programmed computer and a low-pass filter with an appropriate bandwidth WMS-nf (n=1, 2, . . . ) signals, wherein said WMS-nf signals are harmonics of said f,
   c. determining a physical property of said gas sample according to ratios of said WMS-nf signals;
   d. determining in situ a zero-absorption background using scanned-wavelength WMS; and
   e. determining non-absorption losses, wherein said non-absorption losses comprise fluctuations in detected laser beam intensity due to transmission attenuation by optical components, laser beam deflection, laser beam misalignment, light scattering from particles in said gas sample, or light that is not absorbed by molecules using at least two said harmonics without said zero-absorption background determination in environments where collision broadening has blended transition linewidths, wherein calibration free WMS measurements are enabled without determination of said transition linewidth.

2. The method of claim 1, wherein said physical properties of said gas sample are selected from the group consisting of arbitrary species, pressure, and temperature.

3. The method of claim 2, wherein said pressure of said gas sample is determined according to ratios $2f_{peak}/4f_{peak}$ and $2f_{peak}/6f_{peak}$.

4. The method of claim 1, wherein multiple ratios of said harmonic measurements provide simultaneous determination of constituent gas properties selected from the group consisting of a gas number density an absorber mole fraction, a gas pressure, and a gas temperature.

5. The method of claim 1, wherein a first harmonic 1f signal is used to normalize a signal at harmonics greater or equal to 2f to account for said non-absorption transmission losses.

6. The method of claim 1, wherein for scanned-wavelength WMS, a normalization with a mean magnitude of the 0f signal is used, wherein a mean variation on said 0f signal is decreased by averaging.

7. The method of claim 1, wherein a 0f-normalized 1f signal is used to infer gas properties in harsh environments comprising time-varying non-absorption transmission losses.

8. The method of claim 1, a molecular absorbance is determined as a function of time during tuning of said TL.

9. The method of claim 1, wherein both even and odd harmonics of said f are used to determine properties of said gas sample.

10. The method of claim 1, wherein ratios said WMS-nf signals are a function of a transition lineshape of a specific said harmonic at a specific said wavelength, wherein said ratio is independent of an integrated absorbance and a transmitted laser power.

11. The method of claim 1, wherein said physical property comprises a collision width, wherein a total pressure of a gas mixture is proportional to a collision broadening width of said transition lineshape.

12. The method of claim 11, wherein said determination of collision broadening width is enabled for an unknown gas mixture within a condition of optically thin absorption for an isolated transition.

13. The method of claim 1, wherein a ratio of $2f_{peak}$ to $4f_{peak}$ is used to infer a gas temperature, a gas pressure, or a gas composition-dependent collisional width, when said gas properties are unknown, wherein WMS two-line thermometry is used to infer the gas temperature, wherein an absorber mole fraction is determined by either transition used in said two-line thermometry, wherein each said transition has a unique temperature dependent line strength.

* * * * *